United States Patent [19]

Nath

[11] 4,233,493
[45] Nov. 11, 1980

[54] APPARATUS FOR APPLYING INTENSE LIGHT RADIATION TO A LIMITED AREA

[76] Inventor: Günther Nath, 21 Speyererstrasse, Munich, Fed. Rep. of Germany

[21] Appl. No.: 859,143

[22] Filed: Dec. 9, 1977

Related U.S. Application Data

[63] Continuation-in-part of Ser. No. 578,416, May 19, 1975, abandoned.

[30] Foreign Application Priority Data

May 21, 1974 [DE] Fed. Rep. of Germany ....... 2424726
Mar. 13, 1975 [DE] Fed. Rep. of Germany ....... 2511037

[51] Int. Cl.³ .................... H05B 3/02; A61N 5/06; F21V 9/00
[52] U.S. Cl. .................... 219/354; 128/303.1; 128/397; 128/398; 219/85 BA; 219/121 L; 219/347; 219/349; 250/504 R; 350/96.1; 350/96.34; 362/32; 362/294; 362/373; 362/804
[58] Field of Search ............... 219/342, 343, 347–349, 219/354, 85 BA, 85 BM, 85 R, 121 L, 121 LM; 250/494, 495, 503, 504, 510; 128/303.1, 395–399; 350/96.10, 96.26, 96.30, 96.34; 362/32, 373, 804, 294

[56] References Cited

U.S. PATENT DOCUMENTS

| | | | |
|---|---|---|---|
| 2,466,430 | 5/1949 | Hutchison | 219/354 X |
| 3,455,622 | 7/1969 | Cooper | 362/32 X |
| 3,467,098 | 9/1969 | Ayres | 219/349 UX |
| 3,520,055 | 7/1970 | Jannett | 219/349 UX |
| 3,529,117 | 9/1970 | Costello | 219/347 X |
| 3,621,198 | 11/1971 | Herbrich | 219/349 |
| 3,723,697 | 3/1973 | King | 219/85 BA |
| 3,809,072 | 5/1974 | Ersek et al. | 128/397 X |
| 3,848,587 | 11/1974 | McDonald | 350/96.26 X |
| 3,995,934 | 12/1976 | Nath | 350/96.10 |
| 4,009,382 | 2/1977 | Nath | 350/96.26 X |

FOREIGN PATENT DOCUMENTS 2424726 12/1975 Fed. Rep. of Germany ........ 128/303.1
1225956 3/1971 United Kingdom .

*Primary Examiner*—A. Bartis
*Attorney, Agent, or Firm*—Frishauf, Holtz, Goodman & Woodward

[57] ABSTRACT

The apparatus, used for example to stop bleeding by heat coagulation during surgery, comprises a high power incandescent lamp emitting intense radiation high in infrared content enclosed in a housing having a light guide means, such as a solid light pipe, providing a light exit surface. The exit surface of the light guide means is provided with a self supporting stiff and nonpliable polymeric application element having a thickness of at least about 0.1 millimeters or a polymeric coating having the same thickness and physical characteristics, permanently applied to the exit surface or to a transparent end plate positioned adjacent to and protecting said exit surface. The application element or coating, respectively, is made of a polymer such as Teflon, Teflon PFA, Teflon FEP and Teflon PTFE, etc. and is substantially transparent to the radiation emitted by the lamp. The housing is made of a synthetic polymer material loaded with a coloring agent absorbing blue and green light while transmitting infrared radiation, whereby the glare from the lamp is eliminated and the housing is kept from overheating.

36 Claims, 7 Drawing Figures

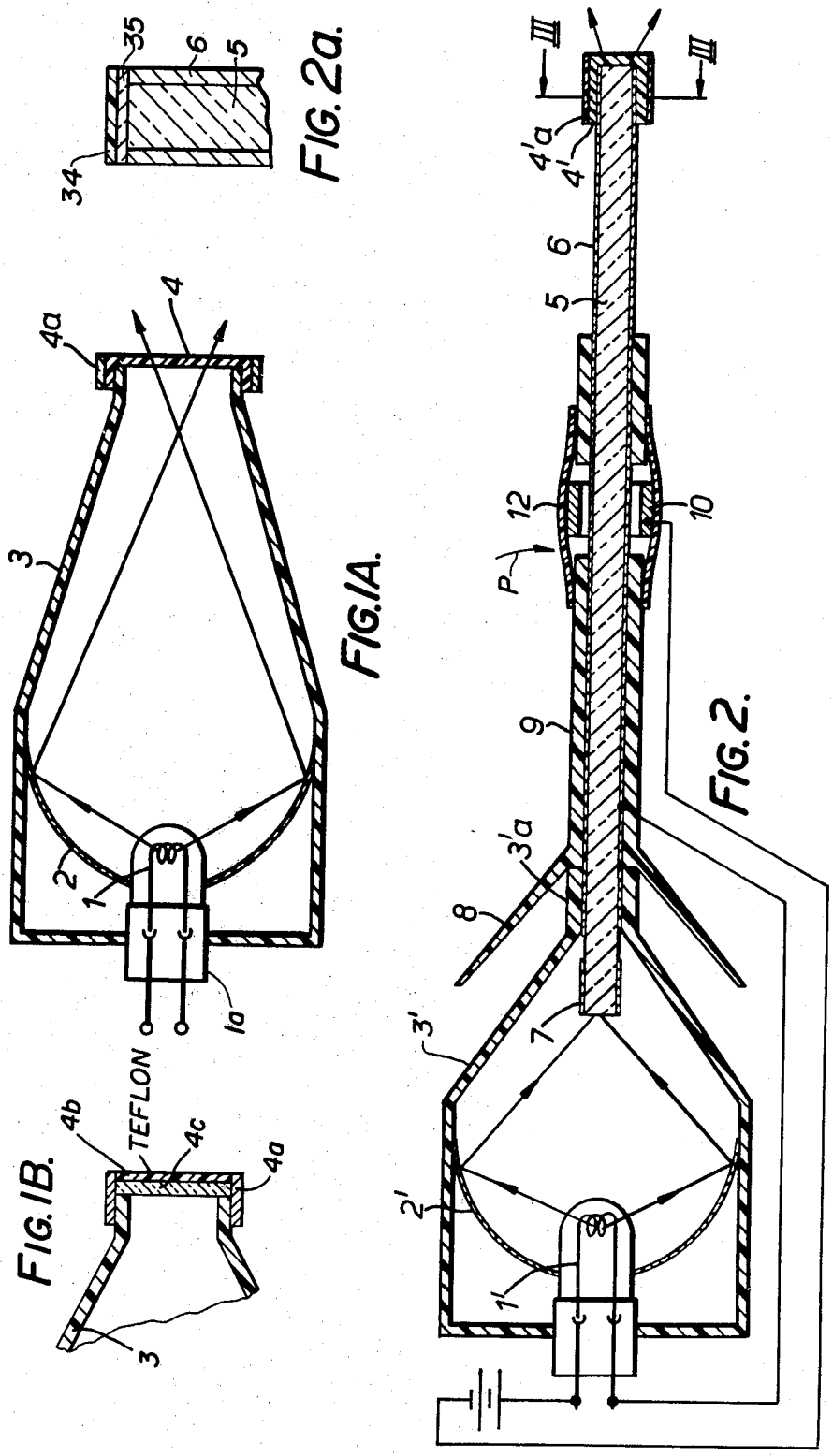

APPARATUS FOR APPLYING INTENSE LIGHT RADIATION TO A LIMITED AREA

The present application is a continuation-in-part application of my earlier application U.S. Ser. No. 578,416, filed May 19, 1975, now abandoned.

The invention relates to an apparatus for applying intense light radiation to a limited area of an object for example to stop bleeding during surgical operations.

The term "light radiation" is intended to include visible light as well as ultraviolet and infrared radiation.

BACKGROUND AND PRIOR ART

Various tasks require the application of intense light radiation to a limited or well-defined area of an object. An example, where the heat produced by the radiation does the job, is, in surgery, stopping hemorrhages by heat-coagulation of a bleeding blood vessel stump.

An example, were the quantum energy of the radiation is the important factor is dentistry, for hardening of polymeric matrix material of a tooth-filling or the like.

Work of the above identified type requires an apparatus which the user can manipulate by hand in a convenient and effortless manner and enables the user to apply the radiation quickly to the exact location where it is needed.

The known apparatus of this type do not meet these requirements for at least one of the following reasons:

The light source housing, which must provide for light and thermal shielding to avoid blinding and burning of the user is bulky.

More important, the light exit surface if brought into contact with the object to be heated, e.g. biological tissue, tends to stick to the object to be heated and becomes contaminated and therefore must be held in a safe distance from the object to be irradiated.

These difficulties greatly impair the ease of handling and make the known apparatus virtually useless for work of the above mentioned type.

SUBJECT MATTER OF THE INVENTION

A light radiation source is located in a housing which has a radiation exit surface from which radiation emitted by said source emerges to an area of utilization.

According to one important aspect of the invention, the light exit surface is formed by an element comprising a polymeric material consisting mainly of the elements carbon and fluorine; or of carbon, fluorine and hydrogen, and in some cases also another halogen and/or oxygen. Polymeric materials of this type are commercially available under the proprietary names Teflon, Teflon FEP, and Teflon PFA.

Materials of this type have a desirable high transmissivity for light radiation in a spectral range including the near ultraviolet and near infrared spectral ranges, can be made to have the structural characteristics of being essentially stiff and non pliable, or can provide firmly adhering coatings on light transmissive substrates made e.g. of glass, quartz or sapphire, and form surfaces having excellent non-sticking properties, especially in a smoothly polished or finished state.

An exit surface of this type can be brought in direct contact with the area to be irradiated, e.g., a stump of a bleeding blood vessel. This applies the radiation directly to the location where it is needed while simultaneously the bleeding can be stopped by mechanical pressure before the radiation is applied. An efficient and quick coagulation is obtained in this way since a maximum of radiation density is obtained at the location where it is needed, while simultaneously the shielding effect of the pool of blood normally present, and the cooling effect of the flowing blood are avoided.

According to an important aspect of the invention, the housing of the light source consists essentially of a polymeric material comprising preferably mainly the chemical elements carbon and fluorine, and a coloring agent absorbing in the blue and green spectral range, where the blinding effect of the light radiation is most annoying, while transmitting red and infrared radiation to allow dissipation of the heat produced by the light source to the surroundings. Since carbon-fluorine polymers transmit optical radiation up to a wavelength of about 8 microns, almost the entire heat-producing radiation of a tungsten incandescent lamp, which is advantageously used as light source, is transmitted by the housing without heating it to such an extent that handling becomes inconvenient or dangerous. Pigments of semiconductive materials having a band-gap corresponding to the yellow and/or red spectral range are preferred as coloring agents, e.g. cadmium sulfide and cadmium telluride. Other suitable materials are cobalt compounds.

Further aspects, features and advantages of the invention will become apparent.

IN THE DRAWINGS

FIG. 1A is a somewhat simplified sectional view of the first embodiment of the invention;

FIG. 1B is a sectional view of a modified light exit window for the device shown in FIG. 1, FIG. 2 is a somewhat simplified sectional view of a second embodiment of the invention comprising a rigid light guide rod;

FIG. 2a is a fragmentary sectional view of an exit window;

Figure 5A:
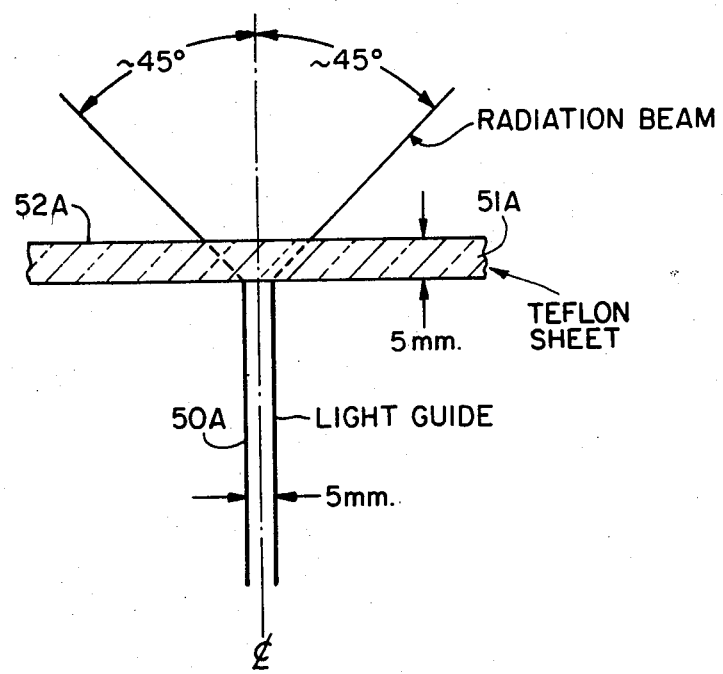
Figure 5B:
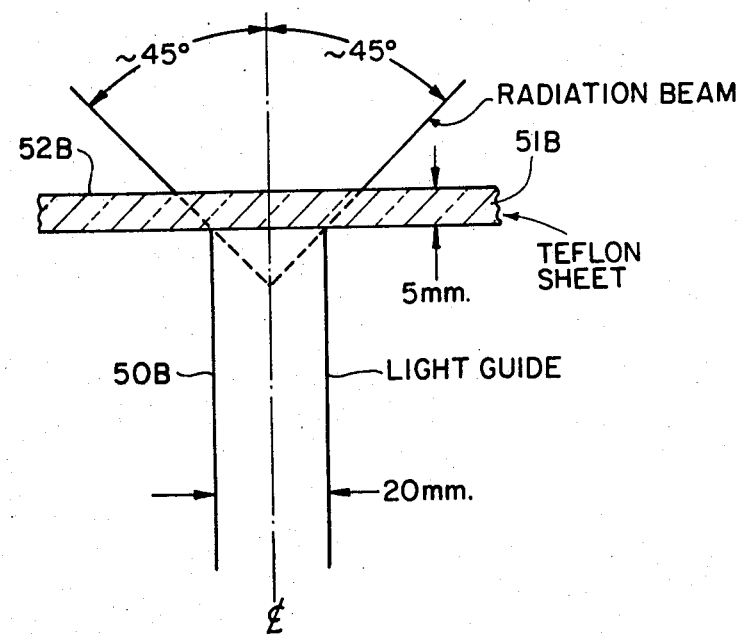

FIGS. 5A and 5B illustrate the relationship of material thickness of the light exit element with respect to the size of the light guide. The embodiment shown in FIG. 1A comprises a light radiation source in form of a tungsten incandescent lamp 1, preferably of the type the bulb of which contains a halogen to avoid blackening. The lamp 1 is provided with an ellipsoidic reflector 2. The lamp 1 and reflector 2 are enclosed by a molded housing 3 of essentially tubular form, one end of which accomodates a lamp socket 1a while the other end forms a radiation exit opening which is closed by a radiation exit window 4 which may have the form of a circular disc, or, as shown the form of a shallow cup held in place by a clamping ring 4a made of metal or another material which is essentially impervious to the radiation emitted by the lamp.

The housing 3 is molded of a polymeric material consisting essentially of a material selected from the group comprising Teflon (a fluorocarbon compound), Teflon PTFE (in full: polytetrafluorethylene), Teflon PFA (a polytetrafluorethylene with perfluoralkoxy side chains $(C_nF_{2n+1}O)$), Teflon FEP (in full: polyperfluorethylene-propylene), and Teflon ETFE (a copolymer of ethylene and tetrafluorethylene, sold by Du Pont under the proprietary name "Tefzel"), so that it transmits electromagnetic radiation of wavelength up to several microns, so that the heat radiation produced by the lamp can be dissipated to the surroundings. To avoid blinding of the user of the apparatus by the visible radiation of the lamp, the material of the housing comprises a coloring agent which absorbs the blue and green, and if necessary also the yellow components of the light emitted by lamp 1. The housing will thus glow red, but since it transmits red and IR radiation, will not heat excessively. The coloring agent may be a semiconductive material having a band-gap corresponding to the yellow and/or red spectral ranges. A suitable material is cadmium sulfide which may be present in an amount of about 0.4% by weight of the polymeric material. Other materials, such as cadmium telluride, or a cobalt compound, such as cobalt oxide, may likewise be used.

The lamp may be a conventional tungsten-halogen-incandescent lamp having a nominal power input of between 50 and 300 watts. Such lamps have a color temperature of approximately 3000° K. and are rich in radiation in the near infrared range.

The window 4 consists preferably of Teflon PFA Teflon or FEP and has, preferably, a smooth, polished outer surface, which is stiff and essentially non resilient. The window material may also comprise a coloring agent of the type mentioned above in connection with the housing. Alternatively, as shown in FIG. 1B, the light exit window may comprise a substrate 4c, e.g. a disc made of quartz, sapphire or heat resistent glass, and a layer 4b made of a non-sticking radiation transmissive, polymer material, such as Teflon FEP or Teflon PFA. The layer 4b may be attached to the substrate disc by suitable mechanical holding means, as a clamping ring 4a, or permanently coated on a surface of the substrate disc 4c.

The embodiment shown in FIG. 2 comprises a tungsten-halogen lamp 1' having a nominal input power preferably between 50 and 300 watts. The lamp 1', and an ellipsoidic reflector 2' associated with the lamp and having a polished gold surface are enclosed in a molded housing 3' which tapers conically to an extension 3'a into which a metal tube 6 enclosing a rigid lightguide rod 5 made of fused quartz is inserted. A sleeve 7 surrounds the light entrance end of rod 5. A middle portion of the metal tube 6 is surrounded by a tubelike member of plastic material forming a handle 9. Adjacent to the housing 3', the member 9 may be provided with a radiation and thermal shield 8 of funnel-like form. The housing 3', the member 9 and the shield 8 may be made of the same type of material as described above with reference to the housing 3 of the embodiment according to FIG. 1A. The housing 3' may have walls 0.5 to 5 mm thick and the material may comprise 0.02 to 2.0% by weight of a coloring agent of the type mentioned in connection with the embodiment of FIG. 1A.

The light exit end of the quartz rod 5 is provided with a cup-like member 4' forming a light exit window and being made of the same type of material as described above with reference to the light exit window 4 of FIG. 1A. The cylindrical portion of member 4' is covered by a sleeve 4'a of strongly absorbing or opaque material, e.g. black or red colored plastic material to avoid blinding. The light exit window is shown as the cup-like member 4', formed as a self-supporting replacable element; the window also can be constructed as described with reference to FIG. 1A and comprise a disc-shaped element of non-sticking, radiation transmissive plastic material as described, or a thin layer applied to, and supported by the end of the light guide system, especially the quartz rod, or more preferably, a separate substrate element similar to the element 4c in FIG. 1B.

Figure 3:
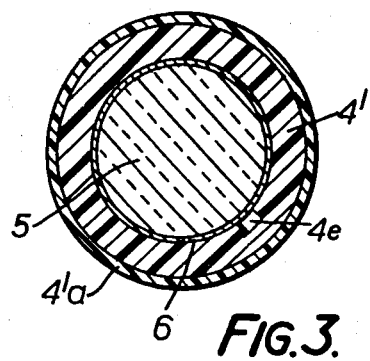
FIG. 3 is a cross section view along the line III—III in FIG. 2.

The self-supporting cup-like member 4', (see FIGS. 2,3) may be formed with an axial slot (FIG. 3) in its inner surface through which air can escape when the member 4' is pushed over the end of the light-guide rod.

The handle 9 or the housing 3' may be provided with an electrical switch for selectively energizing the lamp 1'. This switch advantageously comprises a ring 10 made of electrically conductive material and supported by a sleeve 12 coaxially with and spaced from the metal tube 6. The ring 10 and the metal tube 6 form the cooperating contacts of the switch which are closed by applying pressure as schematically shown by arrow P to the sleeve 12 to move the ring 10 in contact with the metal tube 6. The ring 10 and the metal tube 6 are serially connected by suitable leads in the circuit which supplies electrical energy to the lamp 1'.

Figure 4:
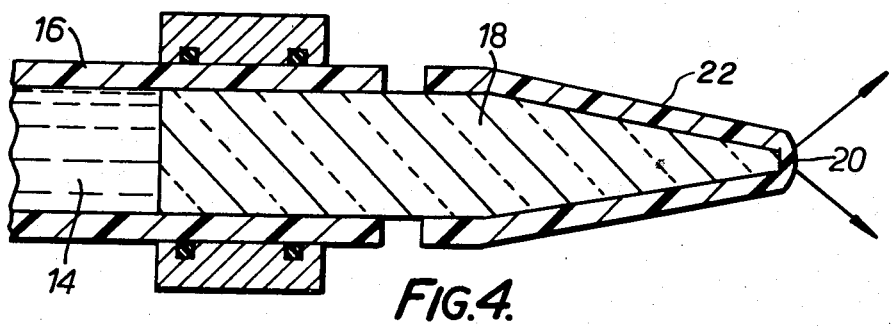
FIG. 4 is a sectional view of a portion of a further embodiment of the invention comprising a flexible light guide.

FIG. 4 shows a portion of an embodiment which may be similar to said shown in FIG. 2 with the exception that the light guide is formed by a column of liquid 14 enclosed in a flexible tube 16 made of Teflon FEP. Shown is the end of the light guide remote to the light source not shown in FIG. 4. The light guide has a light exit structure comprising a quartz rod 18 having a cylindrical end inserted into the tube 16 and having a plane end surface in contact with the column of liquid 14. The other end of the quartz rod 18 tapers to a light exit surface 20 which is covered by a cup-like sleeve 22 which may be a self supporting member or a permanently applied layer of the type as described with reference to member 4' of FIG. 2 or 4 in FIG. 1A.

The member forming the non-sticking radiation exit surface, e.g. the window 4 in FIG. 1A or the layer 4b in FIG. 1B, may be essentially stiff and non pliable and may have a thickness of 0.1 to 0.8 mm, preferably about 0.5 mm. The thickness of the material, if the member formed by the material is self supporting and not permanently coated on a supporting substrate, at the lowest limit, should be such as to prevent deformation of the material upon contact with the surface to which it is applied, that is, to prevent creasing, bending, or closely following the contour surface thereof. A thickness of 0.1 mm appears to be about the lowest limit for such materials which then can be regarded as essentially non-resilient at the end face. The upper limit is determined essentially by the transmissivity of radiation through the material and the power density requirements at the point of application.

Referring to FIGS. 5A and 5B; FIG. 5A shows a light guide 50A with a diameter of 5 mm. A light beam diverges, when emerging from the light guide 50A into the teflon sheet 51A. The angular divergence is approximately 90°. Thus, the spread of the infrared beam at an exit surface 52A of the application element will be approximately 15 mm. That means that the power density of radiation at the surface 52A of the application element dropped for geometrical reasons by a factor of 9. When used as a surgical blood coagulating instrument, therefore, the power density of radiation at the interface of the application element and the tissue at least is nine times lower as compared to the case where the thickness of the application element is very small, for example, 0.1 mm. The minimum power density needed in medical applications of heat applicators of the present type is about 10 to 15 watts per square centimeter, preferably above, say, 30 or 50 W/cm² in case of a surgical coagulation apparatus. Effective coagulation would no longer be possible with a sheet of 5 mm thickness, the tissue merely warming up since the heat input and the transmission efficiency between the radiation source and the light exit surface of the light guide are limited for practical reasons. Thus, for light guides of small diameter, a thickness of the application element which is just thick enough to be consistent with mechanical strength of the element to provide sufficient stiffness so that it can have a smoothly finished surface is preferred.

FIG. 5B shows a light guide 50B of 20 mm diameter, to which a sheet 51B of teflon is applied, having a thickness again of 5 mm. The beam spread at the outer face 52B of the teflon sheet will be about 30 mm. The power density drops only by a factor of about 2.5. This would still permit coagulation with sufficient power input however with longer exposure time as compared to a very thin application element.

All carbon-fluorine polymers attenuate radiation, and especially if the thickness is as high as 5 mm. Thus, even in the case of FIG. 5B, only 50% of the infrared radiation actually is transmitted through the sheet 51B due to the low transparency of carbon-fluorine polymers to radiation. A thickness between 4 to 5 mm appears to be the upper limit for suitable application elements for even the largest diameters of light guides which can be used in medical applications.

The application element, particularly for surgical application, preferably is removable to permit sterilization, or manufacture of the removable elements as a sterile-packed disposable element. For some applications, the application element need not be removable, however, and the light exit application element can be secured to the light guide itself. Removability, or non-removability of the exit element may depend on application of the structure.

Coloring agents used in the materials of the housing and/or the light exit windows may be not only cadmium sulfide and cadmium selenide but also, e.g. cobalt compounds which absorb blue radiation. Other light guides may be used in the apparatus according to the invention, e.g. light guides consisting of a tube having a highly reflecting metal inner surface. Preferably an apparatus according to the invention comprises both a housing and a light exit surface of the types described above, however, apparatus comprising only the housing according to the invention, or comprising only the light exit surface according to the invention may be used with advantage in some applications.

If the light exit surface is used in an apparatus comprising a lightguide, the member forming such surface may be in a direct contact with or spaced from but coupled to and movable with the light exit surface of the light guide. A spaced exit window may be used especially in cases where the radiation penetrating the light exit window has a low divergence angle, e.g. in the case of a laser as light source, and a light-guide as disclosed in my U.S. Pat. No. 3,843,865.

The apparatus according to the invention may comprise a light source other than an incandescent lamp, e.g. a gas discharge lamp, such as a mercury high pressure lamp.

The embodiment described with reference to FIGS. 1 to 4 are especially suited for coagulation purposes in surgery, and curing of polymeric materials in dentistry.

The housing of the light source may also be comprised of other types of carbon-fluorine polymers, as polytrifluorochlorethylene (Kel-F) or other polymers and co-polymers which consist mainly of the elements C, F, other halogens, hydrogen and oxygen. In case of the use of a low power light source e.g. a 50 watt incandescent lamp, the housing may consist also of a polycarbonate polymer comprising a coloring agent suitable to provide the selective transmission properties explained above.

In any of the embodiments described above, the light exit surface (as seen in FIG. 2A), may be formed by a thin layer 34 of the specified polymeric material permanently applied and supported by a plate 35 in form of a disc of a radiation transmissive material, e.g. glass or quartz, or sapphire.

Various change and modifications may be made and features described in connection with any of the embodiments may be used with any of the others, within the scope of the inventive concept.

I claim:

1. Apparatus for applying intense light radiation to a limited area, particularly blood or tissue coagulation apparatus for application to living tissue by direct contact of the apparatus therewith, said apparatus comprising an incandescent lamp emitting intense radiation high in infrared content and forming a light radiation source;

a housing enclosing said light source;

means defining a light exit surface on said housing from which the radiation produced by said source emerges;

a light guide means associated with said housing in light-conducting relation to said source and providing said means defining said light exit surface;

and an application element having a surface for directly contacting said tissue and consisting of a material transparent to infrared radiation emitted by said source; said contacting surface of said application element being formed by a polymeric material consisting essentially of carbon and fluorine; of Teflon ETFE, Teflon PFA, Teflon FEP, Teflon PTFE; or a polymer comprising as main constituents carbon, fluorine and hydrogen, said application element being applied to said light guide means with said contacting surface covering said light exit surface thereby permitting direct application of the radiation from said source through the light guide means and the application element to the tissue, the contacting surface portion of said application element covering said exit surface and adapted to contact the tissue being at least 0.1 mm in thickness and being essentially stiff and non-pliable.

2. An apparatus according to claim 1 wherein a major portion of the wall of said housing is made of a material which absorbs blue and green light, and transmits infrared light.

3. An apparatus according to claim 1, wherein a major portion of the wall of the housing is made of a polymeric selected from the group consisting of a polymer of essentially carbon and fluorine, or a polymer comprising as main constituents carbon, fluorine and hydrogen, said material further comprising a coloring agent dispersed in said polymeric material and having the characteristic of absorbing blue and green light radiation while transmitting red and infrared radiation; the density of the coloring agent dispersed in the major wall portion, and the thickness of said major wall portion being selected to absorb blue and green radiation from the lamp, while transmitting red and infrared radiation from the lamp.

4. An apparatus according to claim 3 wherein said polymeric material of the major wall portion of the housing also includes as a constituent at least one of a halogen other than fluorine; or oxygen.

5. An apparatus according to claim 3 wherein said housing has walls of a thickness between 0.5 and 5 mm and the material of the major wall portion of said housing comprises between 0.02 and 2% by weight of said coloring agent.

6. An apparatus according to claim 1 wherein the application element comprises a removable element applied to said exit surface and having a portion located adjacent to said exit surface and engaging the light guide means.

7. An apparatus according to claim 6 wherein the light guide means has a free end portion adjacent the exit surface;

and said removable application element is in the form of a cup-like member pushed over the free end portion of the light guide means.

8. An apparatus according to claim 6, wherein the removable application element has a disk-like portion having one face adapted to contact said tissue and another face adapted to be in contact with said light guide means.

9. An apparatus according to claim 1 wherein the tissue contacting surface of the application element is smoothly finished.

10. An apparatus according to claim 1 wherein said light source is provided with focusing means to focus said light radiation into a light entrance surface of said light guide means.

11. An apparatus according to claim 1 wherein said light guide means is a solid rod of a material highly transparent to said light radiation.

12. An apparatus according to claim 1 wherein the contact surface of the application element comprises a layer of said polymeric material transparent to the radiation, supported on a transparent plate member; said plate member being made of one of the group consisting of: glass, quartz, or sapphire.

13. An apparatus according to claim 1 wherein the polymeric material of said application element covering said exit surface and adapted to contact the tissue has a thickness of from about 0.1 mm to a value at which the power density of radiation at the contacting surface of said element is not less than about 10 to 15 Watts per square centimeter.

14. An apparatus according to claim 1 wherein the application element comprises a removable element applied to said exit surface in the form of a cup-like member pushed over the free end of the light guide means.

15. Apparatus according to claim 1 wherein the light guide means has a free end portion adjacent the exit surface;

and said application element is a removable cup-like member pushed over the free end portion of the light guide means, the portion of said cup-like member covering said exit surface having a thickness of from about 0.1 mm to about 0.8 mm.

16. Apparatus according to claim 1 wherein the light guide means has a free end portion adjacent the exit surface;

and said application element is a removable cup-like member pushed over the free end portion of the light guide means, the portion of said cup-like member covering said exit surface having a thickness of from about 0.1 mm to a value at which the power density of radiation at the contacting surface of said element is not less than about 15 Watts per square centimeter.

17. Apparatus according to claim 1, further comprising a coloring agent dispersed in said polymeric material transparent to the radiation, said coloring agent absorbing blue and green light radiation while transmitting red and infrared radiation.

18. Apparatus according to claim 1, wherein the polymeric material of said application element adapted to contact the tissue has a thickness of from about 0.1 mm to about 5 mm.

19. Apparatus according to claim 1, wherein the polymeric material of said application element covering said exist surface and adapted to contact the tissue has a thickness of from about 0.1 mm to a value at which the power density of radiation at the contacting surface of said element is not less than about 10 to 15 Watts per square centimeter.

20. Apparatus according to claim 1, wherein the polymeric material of said application element covering said exit surface and adapted to contact the tissue is from about 0.1 mm to about 0.8 mm in thickness.

21. Apparatus according to claim 1, wherein the polymeric material of said application element adapted to contact the tissue has a thickness in the order of about 0.5 mm.

22. Manually holdable apparatus for applying intense light radiation to a limited area of an object, said apparatus comprising a high power lamp emitting intense radiation high in infrared content and forming a light radiation source;

a manually holdable housing enclosing said light source and formed to provide a handle portion to permit manipulation of the housing during use of the apparatus;

and means defining a light exit surface on said housing from which the radiation produced by said source emerges to said object;

wherein a major portion of the wall of said housing is made of a polymeric material selected from the group consisting of a polymer of essentially carbon and fluorine, or a polymer comprising as main constituents carbon, fluorine, and hydrogen, said material further comprising a coloring agent dispersed in said polymeric material and having the characteristic of absorbing blue and green light radiation while transmitting red and infrared radiation;

the density of the coloring agent dispersed in the major wall portion, and the thickness of said major wall portion being selected to absorb blue and green radiation from the lamp, while transmitting red and infrared radiation from the lamp.

23. An apparatus according to claim 22 wherein a light guide is provided carried by the housing and is located between said light radiation source and said light exit surface.

24. An apparatus according to claim 23, wherein said light source is provided with focusing means to focus said light radiation into a light entrance surface of said light guide.

25. An apparatus according to claim 22, wherein said polymeric material of the wall of the housing also includes as a constituent at least one of: halogens other than fluorine or oxygen.

26. An apparatus according to claim 22, wherein said housing has walls of a thickness between 0.5 and 5 mm and the major wall portion material of the housing comprises between 0.02 and 2 percent by weight of said coloring agent.

27. Apparatus for applying intense light radiation to a limited area, particularly blood or tissue coagulation apparatus for application to living tissue by direct contact of the apparatus therewith, said apparatus comprising
an electric lamp emitting intense radiation and forming a light radiation source;
a housing enclosing said light source;
means defining a light exit surface on said housing from which the radiation produced by said source emerges to said tissue;
and an application element covering said light exit surface and having a surface for directly contacting said tissue, said contact surface consisting of a material transparent to infrared radiation emitted by said source; said contact surface being formed by a polymeric material selected from the group consisting of: a polymer consisting essentially of carbon and fluorine; of Teflon ETFE, Teflon PFA, Teflon FEP, Teflon PTFE; or a polymer comprising as main constituents carbon, fluorine and hydrogen and wherein the contact surface of said application element adapted to contact the tissue is formed by a self-supporting disc-shaped member of said polymeric material, said member having a thickness of about at least 0.1 mm and being essentially stiff and non-pliable.

28. An apparatus according to claim 27 further comprising a coloring agent dispersed in said polymeric material transparent to the radiation, said coloring agent absorbing blue and green light radiation while transmitting red and infrared radiation.

29. An apparatus according to claim 28 wherein said coloring agent comprises at least one of the group: consisting of cadmium sulphide, cadmium telluride, or a cobalt compound.

30. An apparatus according to claim 27 wherein the polymeric material of said application element adapted to contact the tissue has a thickness of from about 0.1 mm to about 5 mm.

31. An apparatus according to claim 28 wherein the polymeric material of said application element covering said exit surface and adapted to contact the tissue is from about 0.1 mm to about 0.8 mm in thickness.

32. Apparatus according to claim 28 wherein the polymeric material of said application element adapted to contact the tissue has a thickness in the order of about 0.5 mm.

33. Apparatus according to claim 28 wherein light guide means is provided to couple said light source to said light exit surface.

34. Apparatus according to claim 33 wherein said light guide means has a free light exit end, and said light exit application element forms at least a portion of a cup-shaped member pushed over the free end of said light guide means.

35. Apparatus according to claim 33, wherein said coloring agent comprises at least one of the group consisting of: cadmium sulphide, cadmium telluride, or a cobalt compound.

36. Manually holdable apparatus for applying intense light radiation to a limited area of an object, comprising
a high power incandescent lamp emitting intense radiation high in infrared content and forming a light radiation source;
a housing enclosing said light source;
means defining a light exit surface on said housing from which the radiation produced by said source emerges to said object;
a light guide means associated with said housing in light conducting relation to said source and providing said means defining said light exit surface;
an application element having a surface for directly contacting said object to apply said intense light radiation to the object, said application element consisting of a material transparent to the radiation emitted by said source and comprising essentially polymeric material selected from the group consisting of: a polymer consisting essentially of carbon and fluorine; of Teflon ETFE; Teflon PFA; Teflon FEP; Teflon PTFE; or a polymer comprising carbon, fluorine and hydrogen;
said application element having a disk-like portion defining said contacting surface, said disk-like portion being essentially stiff and non-pliable, having a thickness greater than about 0.1 mm, and being applied to said light guide means adjacent to and covering the exit surface thereof to permit application of radiation from said source through the light guide means and the application element to the object.

* * * * *